United States Patent
Ducharme

(10) Patent No.: US 9,675,613 B2
(45) Date of Patent: *Jun. 13, 2017

(54) METHODS OF COLCHICINE ADMINISTRATION

(71) Applicant: HIKMA PHARMACEUTICALS LLC, Amman (JO)

(72) Inventor: Murray Ducharme, St. Laurent (CA)

(73) Assignee: Hikma Pharmaceuticals LLC (JO)

( * ) Notice: Subject to any disclaimer, the term of this patent is extended or adjusted under 35 U.S.C. 154(b) by 0 days.

This patent is subject to a terminal disclaimer.

(21) Appl. No.: 14/511,703

(22) Filed: Oct. 10, 2014

(65) Prior Publication Data

US 2015/0057359 A1    Feb. 26, 2015

Related U.S. Application Data

(63) Continuation of application No. 13/973,897, filed on Aug. 22, 2013, now Pat. No. 8,927,607.

(60) Provisional application No. 61/867,944, filed on Aug. 20, 2013.

(51) Int. Cl.
| | |
|---|---|
| *A61K 31/506* | (2006.01) |
| *A61K 31/12* | (2006.01) |
| *A61K 31/165* | (2006.01) |
| *A61K 31/4164* | (2006.01) |
| *A61K 31/4196* | (2006.01) |
| *A61K 31/138* | (2006.01) |
| *A61K 31/133* | (2006.01) |

(52) U.S. Cl.
CPC .......... *A61K 31/506* (2013.01); *A61K 31/12* (2013.01); *A61K 31/133* (2013.01); *A61K 31/138* (2013.01); *A61K 31/165* (2013.01); *A61K 31/4164* (2013.01); *A61K 31/4196* (2013.01)

(58) Field of Classification Search
None
See application file for complete search history.

(56) References Cited

U.S. PATENT DOCUMENTS

| | | |
|---|---|---|
| 7,601,758 B1 | 10/2009 | Davis |
| 7,619,004 B1 | 11/2009 | Davis |
| 7,820,681 B1 | 10/2010 | Davis |
| 7,906,519 B2 | 3/2011 | Davis |
| 7,915,269 B2 | 3/2011 | Davis |
| 7,935,731 B2 | 5/2011 | Davis |
| 7,964,647 B2 | 6/2011 | Davis |
| 7,964,648 B2 | 6/2011 | Davis |
| 7,981,938 B2 | 7/2011 | Davis |
| 8,093,296 B2 | 1/2012 | Davis |
| 8,093,297 B2 | 1/2012 | Davis |
| 8,093,298 B2 | 1/2012 | Davis |
| 8,097,655 B2 | 1/2012 | Davis |
| 8,415,395 B1 | 4/2013 | Davis et al. |
| 8,415,396 B1 | 4/2013 | Davis et al. |
| 8,440,721 B2 | 5/2013 | Davis |
| 8,440,722 B2 | 5/2013 | Davis |
| 2011/0190397 A1 | 8/2011 | Davis |

OTHER PUBLICATIONS

Terkeltaub et al. Novel Evidence-Based Colchicine Dose-Reduction Algorithm to Predict and Prevent Colchicine Toxicity in the Presence of Cytochrome P450 3A4/P-Glycoprotein InhibitorsArthritis and Rheumatism (2011), vol. 63, pp. 2226-2237.*
Eberl et al. Role of P-Glycoprotein Inhibition for Drug Interactions Clin Pharmacokinet (2007), vol. 46, pp. 1039-1049.*
Podrid et al. Safety and Tolerability of Long-Term Propafenone Therapy for Supraventricular Tachyarrhythmias. (Am J Cardiol (1996), vol. 78, pp. 430-434.*
Hughes, J., et. al, "Inhibition of P-glycoprotein-Mediated Efflux of Digoxin and Its Metabolites by Macrolide Antibiotics", Journal of Pharmacol Sci., 113, pp. 315-324 (2010), The Japanese Pharmacological Society.
Bachmakov I, et. al., "Characterisation of (R/S)-propafenone and its metabolites as substrates and inhibitors of P-glycoprotein", Naunyn Schmiedebergs Arch Pharmacol. Mar. 2005; 371(3): 195-201. Epub Apr. 15, 2005.
Eberl et al., "Role of Glycoprotein Inhibition for Drug Interactions Evidence from In Vitro and Pharmacoepidemiological Studies", Clin Pharmacokinet, (2007) vol. 46, (12), pp. 1039-1049.
Podrid et al., "Safety and Tolerability of Long-term Propafenone Therapy for Supraventricular Tachyarrhythmias", The American Journal of Cardiology, vol. 78, (1996) pp. 430-434.
Terkeltaub, RA et al; "Novel evidence-based colchicine dose-reduction algorithm to predict and prevent colchicine toxicity in the presence of cytochrome P450 3A4/P-glycoprotein inhibitors"; Arthritis Rheum. Aug. 2011; 63(8): 2226-37. doi: 10.1002/art. 30389.
Hynninen et al. "Effects of the Antifungal Voriconazole and Fluconazole on the Pharmacokinetics of S-(+)- and R-(−)-Ibuprofen" Antimicrobial Agents and Chemotherapy (Jun. 2006), vol. 50, pp. 1967-1972.
Woodland et al. "The Digoxin-Propafenone Interaction: Characterization of a Mechanism Using Renal Tubular Cell Monolayers". JPET (1997), vol. 283, pp. 39-45.
Niel et al. "Colchicine today". Joint Bone Spine (2006), vol. 73, pp. 672-678.
GlaxoSmithKline Highlight prescribing Information Rythmol. (Jun. 2013), pp. 1-25. [Retrieved on Nov. 12, 2013], Retrieved from the internet <http://us.gsk.com/products/assets/us_rythmol.pdf>.
Horn et al., Life-Threatening Colchicine Drug Interactions, Pharmacy Times, p. 111 (May 2006).
Wessler et al., J Am Coll Cardiol, 61(25):2495-2502 (2013).

* cited by examiner

*Primary Examiner* — Kendra D Carter
*Assistant Examiner* — Taina D Matos Negron
(74) *Attorney, Agent, or Firm* — Merchant & Gould, PC

(57) ABSTRACT

The invention provides improved methods for coadministration of colchicine with drugs metabolized by CYP3A4 (anciently referred to as cytochrome P450 isozyme 3A4) or the P-glycoprotein transporter, but not both. The method enables non-toxic coadministration of colchicine and the second drug at their ordinary levels safely and effectively without reducing the dose or frequency for either drug.

13 Claims, 4 Drawing Sheets

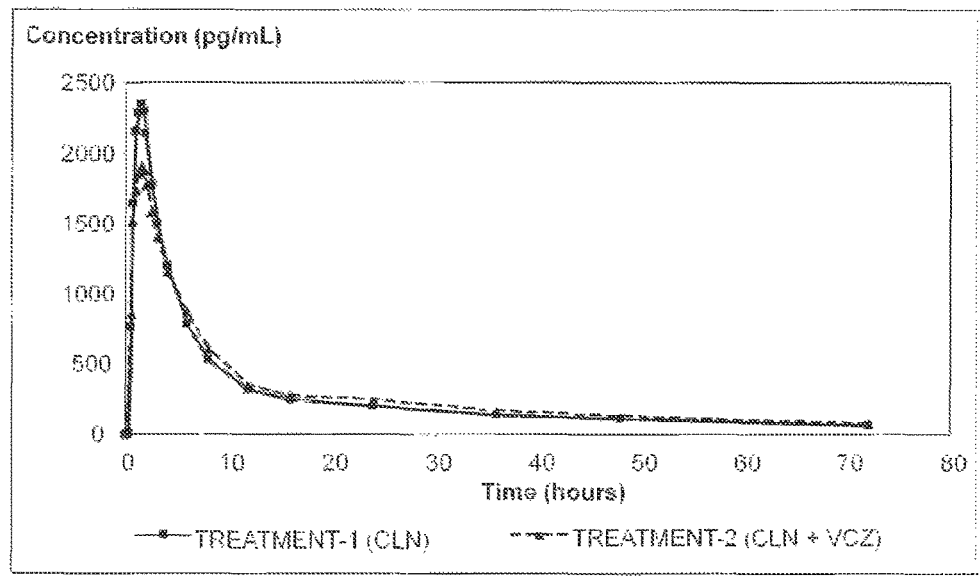
Figure 1. Linear Profile of the Mean Plasma Concentration of Colchicine (CLN) in Coadministration with Voriconazole (VCZ)
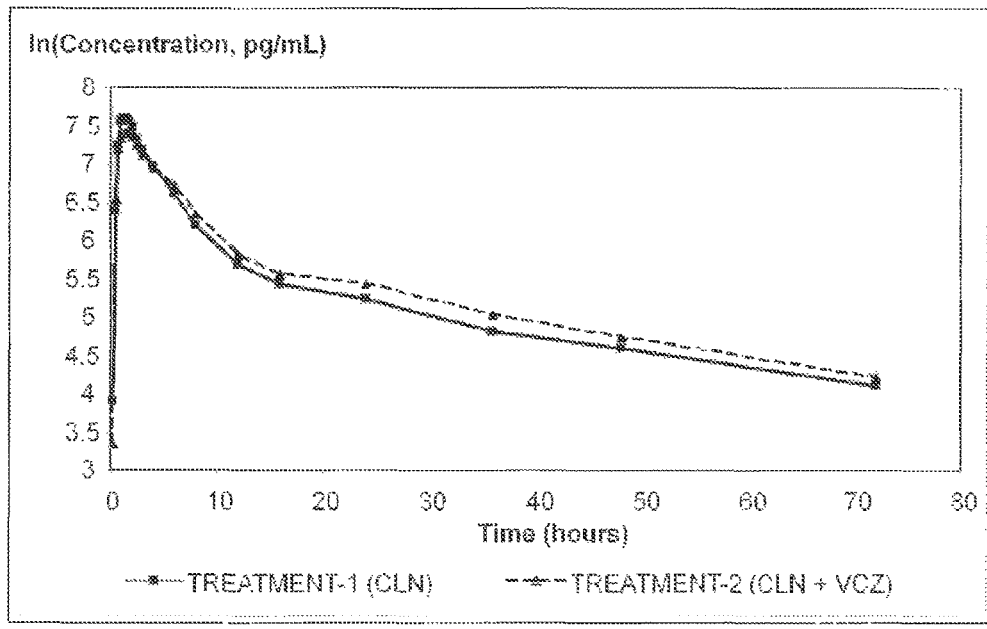
Figure 2. Logarithmic Profile of the Mean Plasma Concentration of Colchicine (CLN) in Coadministration with Voriconazole (VCZ)

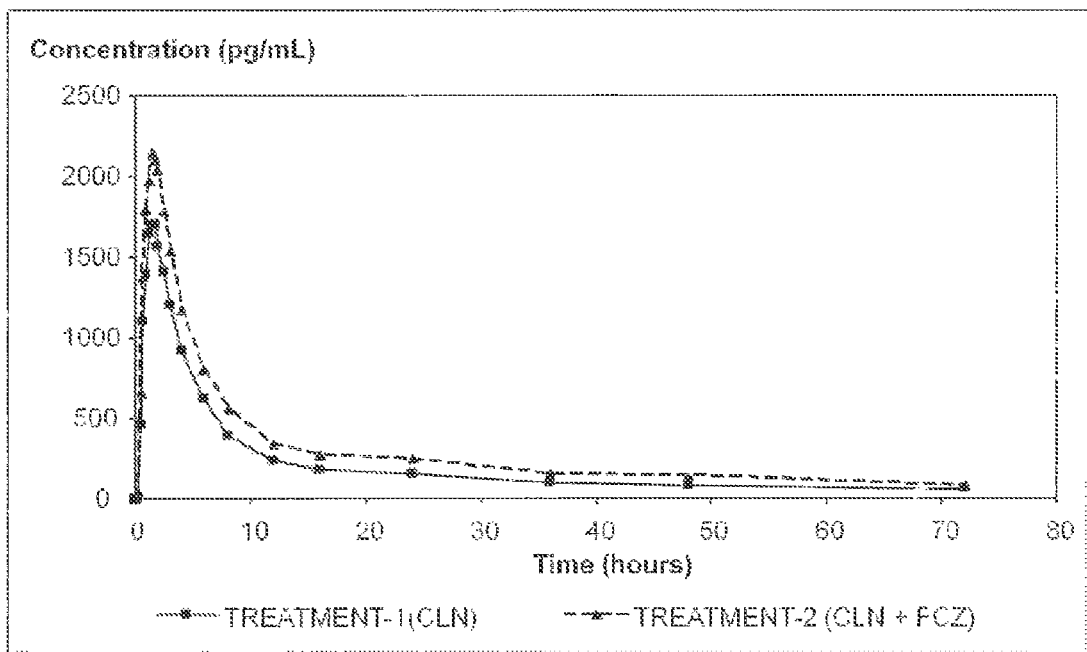
Figure 3. Linear Profile of the Mean Plasma Concentration of Colchicine (CLN) in Coadministration with Fluconazole (FCZ)
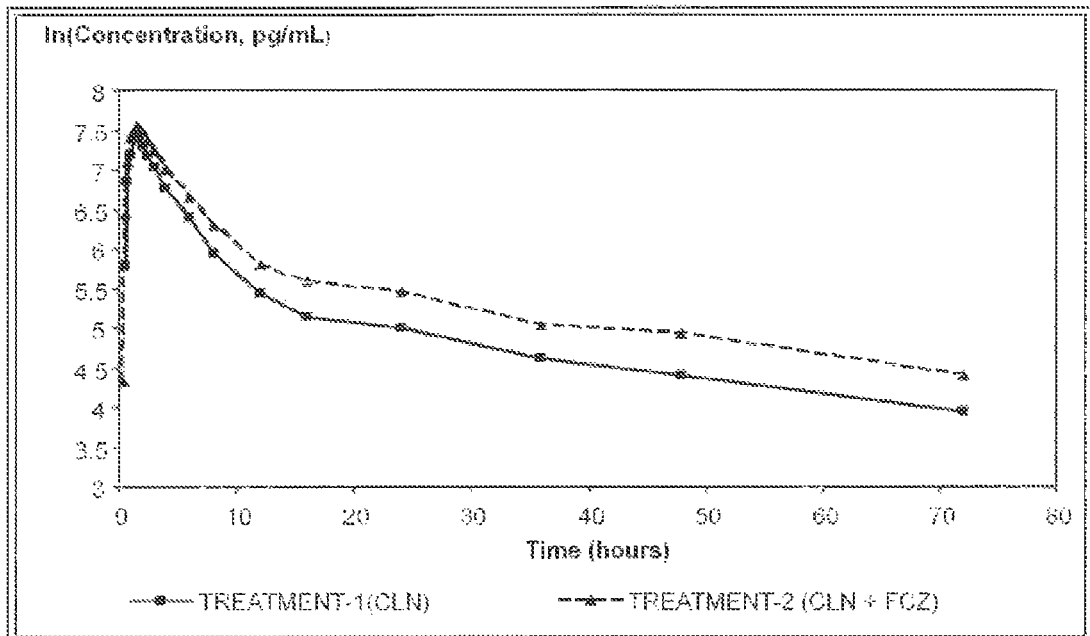
Figure 4. Logarithmic Profile of the Mean Plasma Concentration of Colchicine (CLN) in Coadministration with Fluconazole (FCZ)

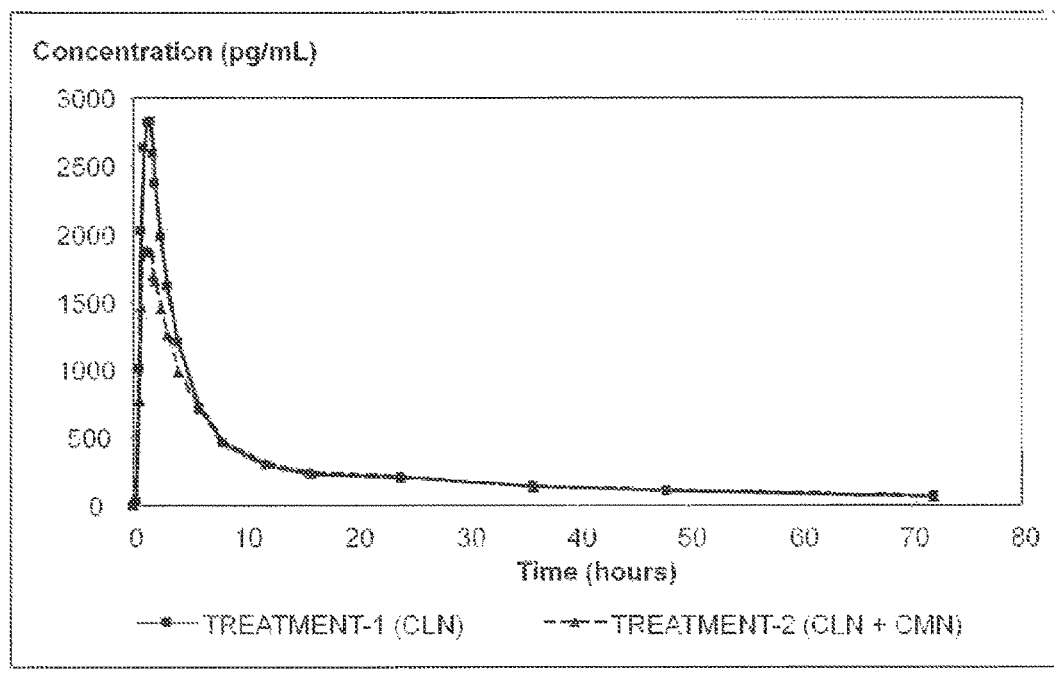
Figure 5. Linear Profile of the Mean Plasma Concentration of Colchicine (CLN) in Coadministration with Cimetidine (CMN)
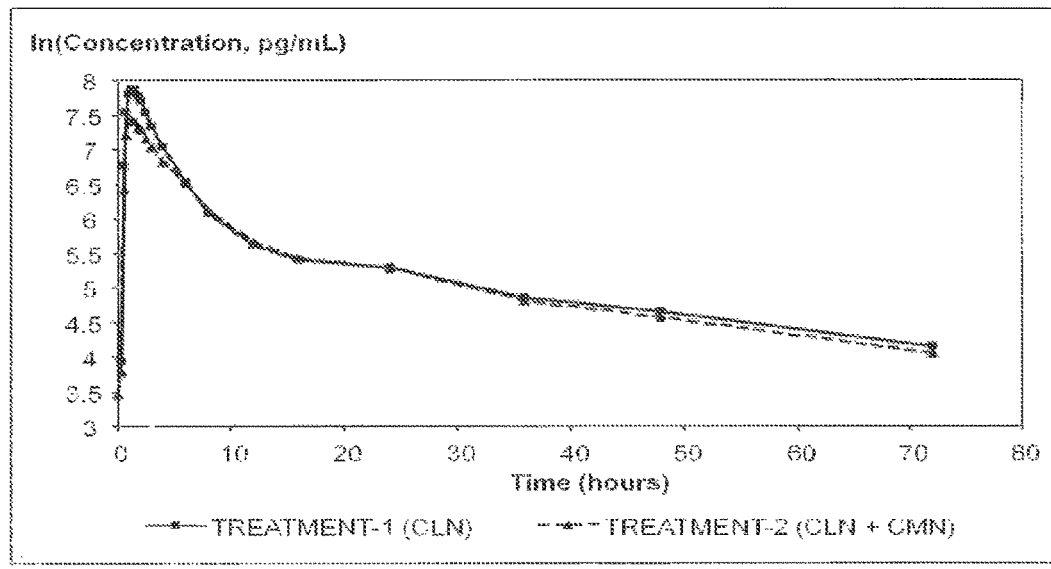
Figure 6. Logarithmic Profile of the Mean Plasma Concentration of Colchicine (CLN) in Coadministration with Cimetidine (CMN)

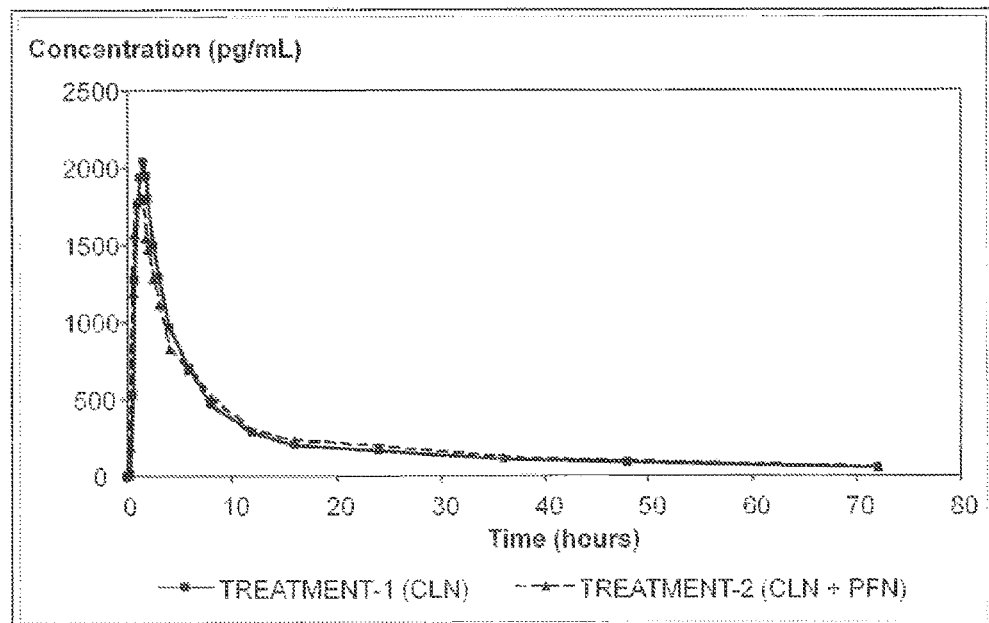
Figure 7. Linear Profile of the Mean Plasma Concentration of Colchicine (CLN) in Coadministration with Propafenone (PFN)
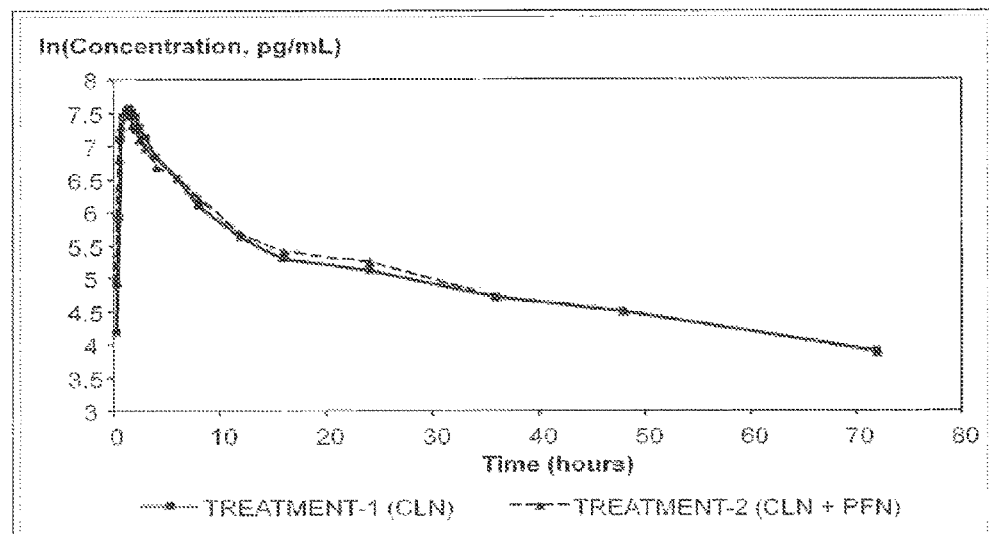
Figure 8. Logarithmic Profile of the Mean Plasma Concentration of Colchicine (CLN) in Coadministration with Propafenone (PFN)

METHODS OF COLCHICINE ADMINISTRATION

CROSS-REFERENCE TO RELATED APPLICATIONS

The present application is a continuation of U.S. application Ser. No. 13/973,897 filed Aug. 22, 2013(now U.S. Pat. No. 8,927,607), which claims the benefit of U.S. Provisional Application No. 61/867,944 filed Aug. 20, 2013, which are herein incorporated by reference in their entirety.

FIELD OF THE INVENTION

This invention relates to methods of administering colchicine for the treatment of inflammatory disorders such as chronic gout, particularly to dosing of colchicine when coadministered with other drugs that share common metabolic pathways, for improved safety and efficacy.

BACKGROUND

Gout, also called gouty arthritis, is a painful inflammatory disorder that arises when uric acid accretes in the joints because it is either overproduced or the kidneys cannot excrete enough. Gout typically manifests as a flare: a sudden, unpredictable and excruciating burning pain with redness, swelling, warmth and stiffness of the joint, sometimes with low fever. The lower extremities and especially the big toe are commonly affected. Gout is an effect of rich diets and is increasingly common: it affects 1-2% of the Western population at some point in their lifetimes.

Colchicine has been used to treat gout for centuries. Colchicine is also the drug of choice for several other debilitating inflammatory disorders, including familial Mediterranean fever, pericarditis, Behçet's disease, immunosuppression, chronic constipation, and other conditions. Colchicine's potential as an anticancer drug is also under investigation.

Colchicine is a tricyclic alkaloid (C22H25NO6; formula weight 399.4) that is present in *Colchicum autumnale* and *Gloriosa superba* as well as other plants. Its chemical structure is depicted below:

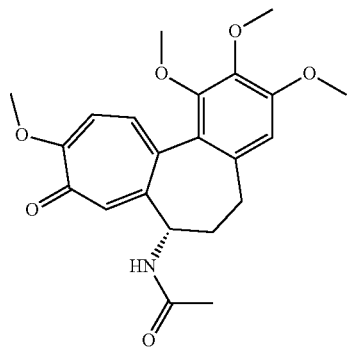

The formal name of the molecule is (S)N-(5,6,7,9-tetrahydro-1,2,3,10-tetramethoxy-9-oxobenzo[alpha]heptalen-7-yl)acetamide. Colchicine is now used to prevent acute flares for chronic gout patients in most parts of the world.

Colchicine's mechanism of action has not yet been fully elucidated but the following is known. Colchicine decreases the inflammatory response to urate crystal deposition by impairing the motility of granular leukocytes. Colchicine also interferes with urate deposition by decreasing lactic acid production by leukocytes. Colchicine also interferes with kinin formation, diminishes phagocytosis and subsequent inflammatory responses, and disrupts microtubules. It also inhibits mitosis, thereby especially affecting cells that have high turnover rates such as in the gastrointestinal tract and bone marrow. Nausea and diarrhea are the primary adverse side effects of colchicine therapy when it is used in a safe dosage range.

Typically Colchicine is administered orally and is rapidly absorbed through the gastrointestinal tract. In patients with normal organ function, peak concentrations in the blood are reached within about 2 hours. Colchicine and its metabolites (mainly 3-demethylcolchicine and 2-demethylcolchicine) distribute to the white blood cells, liver microsomes, kidneys, spleen and intestines. The liver metabolizes colchicine. The compound and/or its metabolites are excreted in feces but up to 20% of colchicine passes unchanged in the urine.

The margin of safety for colchicine doses is narrow, posing a special risk from drug-drug interactions that have the effect of increasing colchicine concentrations in the blood by slowing its metabolism or other elimination. Rhabdomyolysis and in many cases death have been reported when colchicine levels in the blood substantially exceeded clinically recommended levels, particularly in patients who had impaired function of the liver or kidneys.

In individuals whose organ function is impaired colchicine can persist in the body at very high (i.e., toxic) levels for long periods. Moreover a large number of physicians have reported that drug-drug interactions result in sustained toxic levels of colchicine even in patients whose organ function was normal. Two physiological processes require special consideration to maintain colchicine in a safe range in the blood. Firstly, the body's main drug metabolic enzymes for colchicine are from the CYP3A subfamily, especially CYP3A4 present in the liver, gastrointestinal tract, kidney and other sites. The medical consensus is that when a coadministered drug inhibits CYP3A4 activity, colchicine's half-life and bioavailability is greatly increased and toxicity is much more likely if the dose of colchicine is not reduced.

Secondly, P-glycoprotein (P-gp) acts as an efflux pump to evict many xenobiotics—including colchicine—from the inside to the outside of cells in an ATP-dependent way. P-gp is encoded by the multiple drug resistance 1 gene (MDR1), known as the ATP-binding cassette subfamily B member 1 (ABCB1) gene. Medical consensus is that when a coadministered drug inhibits P-gp activity, colchicine's bioavailability should increase because of inhibition of P-gp in the gut, and its half life in the blood may increase because if inhibition of P-gp in the kidney, thereby increasing the likelihood of toxicity.

Numerous articles have suggested that CYP3A4 and P-gp act in concert with one another and are inhibited by many of the same agents. (Z. Yang et al., *J. Pharmacol. Exp. Ther.* 2008; 327:474-81; S. Choudhuri and K. D. Claassen, *Int. J. Toxicol.* 2006; 25:231-59; S. Zhou et al., *Drug Metab. Res.* 2004; 36:57-104; F. Thiebaut et al., *Proc. Natl. Acad. Sci. USA* 1987; 84:7735-8; I. Sugawara et al., *Cancer Res.* 1988; 48:1926-9; V. J. Wacher et al., *Mol. Carcinog.* 1995; 13:129-34; C. Wandel et al., *Cancer Res.* 199; 59:3944-8.) As a consequence, physicians are typically advised not to coadminister any second drug with colchicine if the second drug is known to inhibit either CYP3A4 or P-gp. At a minimum, physicians are encouraged to reduce the dose of colchicine to minimize the risk of toxicity, even though this reduction might lower the dose beyond a therapeutically effective amount.

A leading clinical study on coadministration of CYP3A4 inhibitors with colchicine recommends colchicine's dosage be lower to less than the standard dose (i.e., lower than the dose used when no inhibitor is coadministered) by about 33-75%, and further recommends that administration at the low dosage should be only one half or one third as often as the standard frequency, all to be determined as a function of the strength of inhibition. (R. A. Terkeltaub et al., "Novel evidence-based colchicine dose-reduction algorithm to predict and prevent colchicine toxicity in the presence of cytochrome P450 3A4/P-glycoprotein inhibitors," *Arthritis and Rheumatism,* 2011; 63:2226-2237, 3521). In other words, those authors found that in the aggregate, the total amount of colchicine that may be tolerable over time is as little as one tenth of the total for the standard dose. Unfortunately the adjusted doses of Terkeltaub et al. require an enhanced level of monitoring because the margin for error is small especially for chronic administration.

The FDA has warned that indiscriminate administration of colchicine with CYP3A4 inhibitors or P-gp inhibitors can create life-threatening conditions and an increased number of serious adverse events. (Food and Drug Administration, "Information for healthcare professionals: new safety information for colchicine (marketed as Colcrys); 2009. URL: http://www.fda.gov/Drugs/DrugSafety/PostmarketDrug-SafetyInformationforPatientsandProviders/ucm174382.htm). Unfortunately the constraints on coadministration are particularly severe for gout patients. These individuals are commonly afflicted by obesity, hypertension, heart disease, systemic infections, depression and other conditions. Yet the drugs to be avoided due to the inhibition interactions with CYP3A4 or P-gp are often the most preferred for treating those secondary conditions. Hence the patient need is urgent and ongoing for a method of treatment that provides colchicine conveniently in safe and effective amounts while simultaneously enabling concomitant administration of second drugs that happen to inhibit CYP3A4 or P-gp.

SUMMARY OF THE INVENTION

Whereas the prior art teaches that reductions in colchicine dosing are needed whenever a CYP3A4 inhibitor or P-gp substrate are co-administered with colchicine, the inventors have discovered that several drugs that inhibit only one of CYP3A4 and P-gp but not the other can be coadministered with colchicine without any colchicine dosing reduction. Patients on chronic long-term therapy with colchicine no longer need worry when they must start taking one of these potentially interacting drugs. In addition, they need not suffer drops in colchicine efficacy due to unnecessary and inadvisable dosing reductions.

Therefore, in a first embodiment the invention provides a method of chronically treating a patient for an inflammatory disorder with colchicine while concomitantly administering a second drug that is an inhibitor of CYP3A4 but is not an inhibitor for P-gp, wherein the method comprises:
  a) administering to the patient a therapeutically effective fixed maintenance dose of colchicine in an amount of from about 0.6 to about 1.2 mg/day, for a maintenance period of a plurality of days;
  b) before or after step (a), administering to the patient one or more therapeutically effective doses of the second drug; and
  c) concomitantly with step (b), administering to the patient the fixed maintenance dose of colchicine of step (a) without dose reduction.

In various embodiments, a strong inhibitor of CYP3A4 such as voriconazole, a moderate inhibitor such as fluconazole, or a weak inhibitor such as cimetidine, administered in conventional therapeutically effective doses.

In a second embodiment the invention provides a method of chronically treating a patient for an inflammatory disorder while concomitantly administering a second drug that is an inhibitor of P-gp but is not an inhibitor for CYP3A4, wherein the method comprises:
  a) administering to the patient a therapeutically effective fixed maintenance dose of colchicine in an amount of from about 0.6 to about 1.2 mg/day, for a maintenance period of a plurality of days;
  b) before or after step (a), administering to the patient one or more therapeutically effective doses of the second drug; and
  c) concomitantly with step (b), administering to the patient the fixed maintenance dose of colchicine of step (a) without dose reduction.

In one embodiment the P-gp inhibitor is propafenone, administered in a conventional therapeutically effective dose.

Additional embodiments and advantages of the invention will be set forth in part in the description which follows, and in part will be obvious from the description, or may be learned by practice of the invention. The embodiments and advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

FIG. 1 is a graph of the linear profile of the mean plasma concentration of colchicine (CLN) in coadministration with voriconazole (VCZ).

FIG. 2 is a graph of the logarithmic profile of the mean plasma concentration of colchicine (CLN) in coadministration with voriconazole (VCZ).

FIG. 3 is a graph of the linear profile of the mean plasma concentration of colchicine (CLN) in coadministration with fluconazole (FCZ).

FIG. 4 is a graph of the logarithmic profile of the mean plasma concentration of colchicine (CLN) in coadministration with fluconazole (FCZ).

FIG. 5 is a graph of the linear profile of the mean plasma concentration of colchicine (CLN) in coadministration with cimetidine (CMN).

FIG. 6 is a graph of the logarithmic profile of the mean plasma concentration of colchicine (CLN) in coadministration with cimetidine (CMN).

FIG. 7 is a graph of the linear profile of the mean plasma concentration of colchicine (CLN) in coadministration with propafenone (PFN).

FIG. 8 is a graph of the logarithmic profile of the mean plasma concentration of colchicine (CLN) in coadministration with propafenone (PFN).

DETAILED DESCRIPTION OF THE INVENTION

The invention may be more fully understood by reference to the following definitions.

When the singular forms "a," "an" and "the" or like terms are used herein, they will be understood to include plural referents unless the context clearly dictates otherwise. Thus, for example, reference to "a pharmaceutical carrier" includes mixtures of two or more such carriers, and the like. The word "or" and like terms mean any one member of a particular list and also includes any combination of members of that list.

When used herein the term "about" or "ca." will compensate for variability allowed for in the pharmaceutical industry and inherent in pharmaceutical products, such as differences in product strength and bioavailability due to manufacturing variations and time-induced product degradation. The term allows for any variation which in the practice of pharmaceuticals would allow the product being evaluated to be considered pharmaceutically equivalent or bioequivalent, or both if the context requires, to the recited strength of a claimed product.

Throughout the description and claims of this specification, the word "comprise" and variations of the word, such as "comprising" and "comprises," means "including but not limited to," and is not intended to exclude, for example, other additives, components, integers or steps.

The term "inflammatory disorder" refers to an inflammatory disorder that responds to treatment by colchicine: these include but are not limited to gout (acute or chronic), familial Mediterranean fever (FMF); pericarditis; Behçet's disease; constipation-predominant irritable bowel syndrome; and aphthous stomatitis (canker sores).

The term "flare" refers to an acute attack of a recurring nature.

The terms "acute" and "chronic" have their usual and ordinary meaning in the medical arts, both with respect to the duration, persistence and recurrence of a patient's medical condition and with respect to the duration of treatment.

The terms "treating" and "treatment," when used herein, refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The terms "administer" and "administration" have their usual and ordinary meaning in the art of treating a patient with a drug. The terms "coadministration" and "concomitant administration" as used herein are synonymous and refer to administering two drugs to a patient in such a manner and with such timing that both drugs reside in the patient's body at the same time. The coadministration may be simultaneous or sequential in time, and the coadministered drugs may be administered to a patient at the same time, or separately but near in time, or on the same day, or otherwise in a way that results in substantial overlap of the residence periods for the respective drugs in the body.

The term "maintenance dose" refers to a dose at which colchicine is administered at a fixed dose for a sustained period of time. The term "maintenance period" refers to the duration of time over which maintenance doses are provided; this typically is at least seven consecutive days and may be much longer. The term "fixed" as used with respect to a dose refers to an amount that is relatively constant from one administration episode to the next. The term "therapeutically effective" refers to a dose that is considered sufficient to cause a satisfactory positive improvement in the medical condition being treated, when administered according to the prescribed course of treatment. With respect to colchicine a particularly preferred range for fixed maintenance doses is an amount of from 0.6 mg/day to about 1.2 mg/day but the invention is not so limited, and can range from 0.3 or 0.6 mg/day to 1.8 or 2.4 mg/day.

With respect to voriconazole a preferred therapeutically effective oral dose is from about 100 or 200 mg/day to about 400, 600 or 800 mg/day but the invention is not so limited. With respect to fluconazole a particularly preferred therapeutically effective oral dose is from about 50, 100, or 200 mg/day to about 400 mg/day but the invention is not so limited. With respect to cimetidine a particularly preferred therapeutically effective oral dose is from about 200, 400, 600 or 800 mg/day to about 1,200, 1,600, or 2,000 mg/day but the invention is not so limited. With respect to propafenone a particularly preferred therapeutically effective oral dose is from about 300 or 450 mg/day to about 675 or 900 mg/day but the invention is not so limited.

In any of the foregoing embodiments, the potentially interacting drug can be administered as the free base or a pharmaceutically acceptable salt thereof.

"Pharmaceutically acceptable salts" means salts that are pharmaceutically acceptable, as defined below, and that possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed when an acidic proton present is capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

The term CYP (previously known as "cytochrome P450") refers to the liver's family of metabolic enzymes, as are known to practitioners of the art. The terms CYP3A and CYP3A4 refer to a subfamily of enzymes and to a particular enzyme, respectively.

The term "P-glycoprotein" (P-gp) refers to the protein encoded by the multiple drug resistance 1 gene (MDR1), which gene is also known as the ATP-binding cassette subfamily B member 1 (ABCB1) gene. P-gp is to be understood here as an ATP-dependent pump for transporting drug molecules out of cell interiors.

The terms "inhibitor", "inducer", "substrate", "enzyme", "isozyme" (the latter being synonymous with "isoenzyme"), and "molecular pump" have their usual and ordinary meaning in biochemistry for describing the effects of drug molecules on the activity of enzymes and molecular transport proteins in human bodies, but with the following qualifications. The term inhibitor as used herein includes both compounds that prevent binding of another molecule to an enzyme or molecular pump and compounds that cause downregulation of the enzyme or molecular pump. Similarly the term inducer as used herein includes both compounds that facilitate binding of another molecule to an enzyme or molecular pump and compounds that cause upregulation of the enzyme or molecular pump. The FDA's definition is used here for the relative strength of CYP3A4 inhibitors regarding their effect on a CYP3A4 substrate drug with which the respective inhibitor is coadministered. "Strong inhibitors" cause ≥5-fold (i.e., 400%) increase in AUC (area under curve over time for substrate drug concentration in the blood) or ≥80% decrease in oral clearance rate. "Moderate inhibitors" cause ≥2-fold but <5-fold (i.e., 100-399%) increase in AUC or 50-80% decrease in oral clearance rate. "Weak inhibitors" cause ≥1.25-fold but <2-fold (i.e., 25-99%) increase in AUC or 20-50% decrease in oral clearance rate. Likewise the FDA's definition is used here for the relative strength of P-gp inhibitors: the FDA classifies drugs as being merely inhibitors (i.e., causing ≥25% increase in AUC of a substrate compound) or non-inhibitors. (See Tables 4, 5, and 14 and their respective headers and notes at http://www.fda.gov/drugs/developmentapproval-process/developmentresources/druginteractionslabeling/ucm093664.Htm#potency).

Lists of inhibitors, inducers and substrates for CYP3A4 and P-gp can also be found, for instance, at http://www.pharmacologyweekly.com/content/pages/online-drug-therapy-tables, http://youscript.com/P-gp-table/, http://www.edhayes.com/CYP450-2.html, http://www.genemedrx.com/Cytochrome_P450_Metabolism_Table.php, and other sites.

The term "dual inhibitor" as used herein refers to a compound that inhibits both CYP3A4 and P-gp in the human body. Examples of dual inhibitors include but are not limited to amiodarone, biricodar, bocepravir, clarithromycin, cyclosporine, darunavir, diltiazem, dronedarone, erythromycin, fenofibrate, fluoxetine/norfluoxetine, fluvoxamine, grapefruit juice (and its bergamottin content), itraconazole, josamycin, ketoconazole, lovastatin, metronidazole, mibefradil, mifepristone, nefazodone, nicardipine, nifedipine, piperine, posaconazole, quercetin, quinine, ritonavir, saquinavir, tacrolimus, telaprevir, telithromycin, and verapamil.

The term "single inhibitor" as used herein refers to a compound that inhibits one of CYP3A4 or P-gp in the human body but not both. Examples of single inhibitor compounds that inhibit CYP3A4 but not P-gp include but are not limited to aprepitant, buprenorphine, cafestol, chloramphenicol, cimetidine, ciprofloxacin, danazol, delavirdine, fluconazole, imatinib, midazolam, norfloxacin, and voriconazole, as well as extracts from the following botanical species *Allium sativum, Ammi visnaga, Azadirachta indica, Cimicifuga racemosa, Harpagphytum procumbens, Hydrastis Canadensis*, naringenin compounds (e.g., from grapefruit), *Panax ginseng, Panax quinquefolius, Strychnos ligustrina* and *Uncaria tomentos*. Examples of single inhibitor compounds that inhibit P-gp but not CYP3A4 include but are not limited to alfentanil, amitripyline, astemizole, atorvastatin, azelastine, bepidil, bromocriptine, carbamazepine, carvedilol, chloroquine, chlorpromazine, digoxin, disulfiram, doxazosin, elacridar, emetine, felodipine, fentanyl, FK506, fluphenazine, gallopamil, garlic extract, haloperidol, imipramine, ivermectin, lidocaine, loratadine, methadone, nobilitin, norverapamil, progesterone, propafenone, propranolol, quinidine, reserpine, simvastatin, terfenadine, valinomycin, valspodar and vinblastine.

The terms "mean", "geometric mean", "least squares means" (LSmeans), "confidence limits" (CI, expressed in units of %), and "coefficient of variation" (C.V., expressed in units of %), have their usual and ordinary meaning for clinical statistics and are well known to practitioners of the pharmaceutical arts in descriptors of pharmacokinetic parameters.

The term "$C_{max}$" (expressed in units of pg/mL) means maximum observed plasma concentration and refers herein to that of colchicine. The term "$\ln(C_{max})$" means the natural logarithm of the numerical value of $C_{max}$.

The term "$T_{max}$" (expressed in units of hours, or as a median number of hours for $T_{max}$ in the study population) means the observed time to reach $C_{max}$ following drug administration; if it occurs at more than one time point $T_{max}$ is defined as the first time point with this value.

The term "$AUC_T$" (expressed in units of pg·h/mL) means the cumulative area under the plasma time concentration curve (AUC) calculated using the trapezoidal method from time 0 to the time of the last observed quantifiable plasma concentration ($T_{LQC}$). The term "$\ln(AUC_T)$" means the natural logarithm of the numerical value of $AUC_T$.

The term "$AUC_\infty$" (expressed in units of pg·h/mL) means AUC from time 0 to infinity as extrapolated. The term "$\ln(AUC_\infty)$" means the natural logarithm of the numerical value of $AUC_\infty$.

The term "$AUC_{T/\infty}$" (expressed in units of %) means the relative percentage of $AUC_T$ with respect to $AUC_\infty$.

The term "$K_{el}$" (expressed in units of hours$^{-1}$) means the apparent terminal rate constant, estimated by linear regression of the terminal linear portion of the log concentration versus time curve.

The term "$T_{1/2el}$" (expressed in units of hours) means the terminal half life, often assumed to be the half life of elimination.

The term "$CL_{TOT}/F$" (expressed in units of L/h) means the oral clearance, and is calculated as the dose divided by $AUG_\infty$ following oral administration.

The term "$V_D/F$" (expressed in units of L) means the apparent volume of distribution, and is calculated as the dose divided by the value of ($K_{el} \times AUC_\infty$) following oral administration.

The terms "voriconazole", "fluconazole", "cimetidine" and "propafenone" refer to the respective compounds known by those names in the pharmaceutical arts, as shown below.

| Common Name and Trade Name(s) (and Source(s)) | IUPAC Name | Chemical Structure |
|---|---|---|
| Voriconazole<br>VFEND ® (Pfizer) | (2R,3S)-2-(2,4-difluorophenyl)-3-(5-fluoropyrimidin-4-yl)-1-(1H-1,2,4-triazol-1-yl)butan-2-ol | |
| Fluconazole<br>Diflucan ®; Trican ® (Pfizer). | 2-(2,4-difluorophenyl)-1,3-bis(1H-1,2,4-triazol-1-yl)propan-2-ol | |
| Cimetidine<br>Tagamet ®; Tagamet HB ®; Tagamet HB200 ® (GlaxoSmithKline) | 2-cyano-1-methyl-3-(2-[(5-methyl-1H-imidazol-4-yl)methylthio]ethyl)guanidine | |
| Propafenone<br>Rythmol SR ® or Rytmonorm ® (Knoll; Abbott; Reliant Pharmaceuticals) | 1-{2-[2-hydroxy-3-(propylamino)propoxy]phenyl}-3-phenylpropan-1-one | |

As used herein with respect to drugs, the terms "extended-release" (ER, XR or XL), "timed-release" (TR), "sustained-release" (SR), "sustained-action" (SA), "controlled release" (CR), "modified-release" (MR) and "continuous-release" (Contin) refer to oral dosage forms (typically tablets or capsules) whose formulation and/or dosage form is designed to release the drug more slowly and steadily into the bloodstream over time than an immediate-release (IR) dosage form of the same drug. As used herein with respect to drugs, the term "immediate-release" (IR) refers to a drug for which the formulation and dosage form are not designed to delay dissolution or absorption of the drug into the body when orally administered.

When ranges are given by specifying the lower end of a range separately from the upper end of the range, it will be understood that the range can be defined by selectively combining any one of the lower end variables with any one of the upper end variables that is mathematically possible.

Discussion

As discussed above, for several years the expert consensus has been that the removal of colchicine by CYP3A4 and P-gp is additive. I.e., it has been believed that if either of CYP3A4 or P-gp is inhibited then colchicine concentrations in the blood rise because the other has a limited capacity to increase its own rate of colchicine removal. This view has been reinforced by the observation that administration of colchicine is tolerated within only a narrow dosing window, even in patients who have no ailment other than gout and who receive no drug other than colchicine.

The inventors have now discovered that single inhibitors of CYP3A4 and P-gp do not lead to greatly increased build-up of colchicine in the body, unlike dual inhibitors, and do not necessitate a reduction in colchicine dose when coadministered with colchicine.

Therefore, in one embodiment the invention provides a method of chronically treating a patient for an inflammatory disorder with colchicine while concomitantly administering a second drug that is an inhibitor of CYP3A4 but is not an inhibitor for P-gp, wherein the method comprises: (a) administering to the patient a therapeutically effective fixed maintenance dose of colchicine in an amount of from about 0.6 to about 1.2 mg/day, for a maintenance period of a plurality of days; (b) before or after step (a), administering to the patient one or more therapeutically effective doses of the second drug; and (c) concomitantly with step (b), administering to the patient the fixed maintenance dose of colchicine of step (a) without dose reduction.

The CYP3A4 inhibitor can be a strong, moderate or weak inhibitor. A particularly suitable strong inhibitor is voriconazole. Voriconazole is a synthetic broad-spectrum antifungal agent available in scored white tablets, each containing 200 mg voriconazole base for oral administration. Voriconazole tablets are indicated for the treatment of the following systemic fungal infections: candidiasis, chronic mucocutaneous candidiasis, oral thrush, candiduria, blastomycosis, coccidioidomycosis, histoplasmosis, chromomycosis, and paracoccidioidomycosis. Voriconazole is a strong inhibitor of the CYP3A4 isozyme. Co-administration of colchicine (being primarily metabolized by the CYP3A4 enzyme) with a second drug such as voriconazole has been thought by many to result in increased plasma concentrations of colchicine that could increase or prolong both therapeutic and adverse side effects. However typical maintenance dose ranges of about 200 mg/day to about 400 mg/day of voriconazole may be safely coadministered with typical maintenance dose ranges of from about 0.6/day to about 1.2 mg/day of colchicine.

A particularly suitable moderate inhibitor is fluconazole. Fluconazole is a synthetic broad-spectrum antifungal agent available in scored white tablets, each containing 200 mg fluconazole base for oral administration. Fluconazole tablets are indicated for the treatment of the following systemic fungal infections: candidiasis, chronic mucocutaneous candidiasis, oral thrush, candiduria, blastomycosis, coccidioidomycosis, histoplasmosis, chromomycosis, and paracoccidioidomycosis. Fluconazole is a strong inhibitor of the CYP3A4 isozyme. Co-administration of colchicine (being primarily metabolized by the CYP3A4 enzyme) with a second drug such as fluconazole has been thought by many to result in increased plasma concentrations of colchicine that could increase or prolong both therapeutic and adverse side effects. However typical maintenance dose ranges of about 200 mg/day to about 400 mg/day of fluconazole may be safely coadministered with typical maintenance dose ranges of from about 0.6/day to about 1.2 mg/day of colchicine.

A particularly preferred weak inhibitor is cimetidine. Cimetidine is a synthetic drug that inhibits stomach acid production. It is used to treat heartburn and peptic ulcers and is sold by Prestige Brands (formally by GlaxoSmithKline under the trade name Tagamet and variants of that name. Cimetidine has also been advocated for use to treat several dermatological diseases. Common dosage regimes in adults include the following: oral (800 mg to 1600 mg once a day at bedtime, or 300 mg four times per day, with meals and at bedtime, or 400 mg twice daily, in the morning and at bedtime); and parenteral (300 mg IV or IM every 6 to 8 hours, or a continuous IV infusion at a rate of 37.5 to 50 mg/hour, or up to a maximum rate of 100 mg/hour (2.4 g/day). For dyspepsia doses in patients age 12 or over the dose is commonly 200 mg orally up to 30 minutes before eating with no more than 2 doses per 24 hours. Pediatric doses are commonly as follows: neonatal (5 to 10 mg/kg/day administered IV or IM in divided doses every 8 to 12 hours), infant (10 to 20 mg/kg/day administered IV, IM, or oral in divided doses every 6 to 12 hours); and children 20 to 40 mg/kg/day administered IV, IM, or oral in divided doses every 6 hours). Cimetidine in a maintenance dose may be safely coadministered chronically with typical maintenance dose ranges of from about 0.6/day to about 1.2 mg/day of colchicine.

Another embodiment relates to the coadministration of colchicine with molecules that are P-gp inhibitors but not CYP3A4 inhibitors. In this embodiment the invention provides a method of chronically treating a patient for an inflammatory disorder while concomitantly administering a second drug that is an inhibitor of P-gp but is not an inhibitor for CYP3A4, wherein the method comprises: (a) administering to the patient a therapeutically effective fixed maintenance dose of colchicine in an amount of from about 0.6 to about 1.2 mg/day, for a maintenance period of a plurality of days; (b) before or after step (a), administering to the patient one or more therapeutically effective doses of the second drug; and (c) concomitantly with step (b), administering to the patient the fixed maintenance dose of colchicine of step (a) without dose reduction.

Propafenone is a particular P-gp inhibitor that does not inhibit CYP3A4 for use in the invention. Propafenone is a synthetic drug that is currently sold by Reliant Pharmaceuticals under the brand names Rythmol SR® and Rytmonorm®. It is an anti-arrhythmic medication for the treatment of illnesses associated with rapid heart beats, e.g., atrial and ventricular arrhythmias. The dosage of propafenone varies considerably as a function of the clinical presentation of arrhythmia. About 900 mg/d is generally deemed the maximum safe dosage. Typical treatment begins with a high dosage (about 450-900 mg/d) and decreases to a maintenance dose range of about 300 mg/d (e.g., a maintenance dose range of between 225 and 450 mg/day). Propafenone in a maintenance dose may be safely coadministered chronically with typical maintenance dose ranges of from about 0.6/day to about 1.2 mg/day of colchicine.

In either of the foregoing embodiments, the plurality of days in which the maintenance dose of colchicine is administered can extend 3, 7, 14, 28, or even more days. In like manner, the P-gp inhibitor or CYP3A4 inhibitor can be administered a single day or a second plurality of days, extending 2, 3, 5, 7, 10, 15 or more days.

In any of the foregoing embodiments, the colchicine is preferably administered orally, as in a capsule, tablet or oral suspension. The single inhibitor can be administered via any route of administration, but is also preferably administered orally.

EXAMPLES

The invention may be further understood by consideration of the following illustrative Examples. Example 1 is a comparative example of prior art methods in which dual inhibitors of CYP3A4 and P-gp were coadministered with colchicine and the pharmacokinetics of colchicine evaluated. Examples 2, 3, 4, 5 and 6 exemplify the present invention, and evaluate the pharmacokinetics of colchicine when single inhibitors of CYP3A4 or P-gp are coadministered.

Example 1: Comparative Example for Dual Inhibitors

This Example summarizes the methods and data from R. A. Terkeltaub et al., "Novel evidence-based colchicine dose-reduction algorithm to predict and prevent colchicine toxicity in the presence of cytochrome P450 3A4/P-glycoprotein inhibitors," *Arthritis and Rheumatism*, 2011; 63:2226-2237, 3521 (erratum). To facilitate comparison with subsequent Examples of the present invention, Terkeltaub et al's empirical values are provided in the same units employed there and in a similar sequence and format.

Drug-drug interaction trials were conducted with seven drugs coadministered with colchicine. Six of those drugs (cyclosporine, clarithromycin, ketoconazole, ritonavir, verapamil ER, and diltiazem ER) are dual inhibitors known to substantially inhibit both CYP3A4 and P-gp. The seventh tested drug (azithromycin) was at most marginal in both functions: depending on the publication it is described as a weak inhibitor or non-inhibitor for CYP3A4 and also depending on the publication it is described as an inhibitor or a non-inhibitor for P-gp. Each trial was an open-label, drug interaction study to investigate the effects of multiple-dose dual inhibitors on single-dose pharmacokinetics of colchicine in healthy male volunteers. The trial was a single center, non-randomized, open-label, one-sequence, two period drug-drug interaction (DDI) study.

The diagnosis and main criteria of inclusion were: male and female volunteers from white, black or another race; non-smokers; at least 18-45 years of age; with a body mass index of 18-32 kg/m² and no concomitant use of medications or other products that might interfere with the interpretation of pharmacokinetic results from the studies. Subjects were in good health as determined by a medical history, physical examination, measurement of vital signs and clinical laboratory testing.

The treatment protocols each included two colchicine administrations separated by a wash-out period so as to obtain representative blood concentration values with and without the presence of the second drug. Each study began with 24 subjects; some subjects withdrew but for reasons unrelated to adverse health effects.

Cyclosporine: colchicine (0.6 mg) was administered on days 1 (fasted state in the morning) and 15, and cyclosporine (100 mg once) was administered on day 15. (23 subjects completed the study).

Clarithromycin: colchicine (0.6 mg) was administered on days 1 (fasted state in the morning), 22 and 29, and clarithromycin 250 mg (administered twice daily) was administered on days 22-29. (23 subjects completed the study).

Ketoconazole: colchicine (0.6 mg) was administered on days 1 (fasted state in the morning) and 19, and ketoconazole (200 mg twice daily). (24 subjects completed the study).

Ritonavir: colchicine (0.6 mg) was administered on days 1 (fasted state in the morning) and 19, and ritonavir (100 mg twice daily) was administered on days 15-19. (17 subjects completed the study).

Verapamil ER: colchicine (0.6 mg) was administered on days 1 (fasted state in the morning) and 19, and verapamil ER (240 mg once daily) was administered on days 15-19. (24 subjects completed the study).

Diltiazem ER: colchicine (0.6 mg) was administered on days 1 (fasted state in the morning) and 21, and diltiazem ER (240 mg once daily) was administered on days 15-21 (total of 7 doses). (20 subjects completed the study).

Azithromycin: colchicine (0.6 mg) was administered on days 1 (fasted state in the morning) and 19, and azithromycin 500 mg (2×250 mg) was administered on day 15, and 250 mg (once daily) was administered on days 16-19. (21 subjects completed the study).

The blood of the subjects was collected in 34 samples each as follows: for the colchicine administration on Day 1 (denoted here as Treatment-1) and on an end day (denoted here as Treatment-2) for colchicine administration (i.e., after a wash-out period), a blood sample was collected prior to and 0.5, 1, 1.5, 2, 2.5, 3, 4, 6, 8, 12, 16, 24, 36, 48, 72 and 96 hours after colchicine administration.

The colchicine content of human plasma was analyzed by HPLC with LC/MS/MS detection and an assay range of 200-40,000 pg/mL.

Safety was evaluated through assessment of adverse events and other criteria.

The pharmacokinetic (PK) parameters of these trials were (as stated in the notation of the remaining Examples in the present application) $C_{max}$, $AUC_T$, $AUC_\infty$, $T_{max}$, $K_{el}$, $T_{1/2el}$, $Cl_{TOT}/F$ and $Vd/F$. Statistical analysis of the pharmacokinetic parameters employed arithmetic means and were based on a 90% confidence interval of the ratio of geometric means for the $C_{max}$, $AUC_T$, $K_{el}$, $T_{1/2el}$ and $Cl_{TOT}/F$. Safety was determined by descriptive statistics.

A summary of the safety results follows in Table 1. The pharmacokinetic parameters are summarized in Tables 2, 3, 4, 5, 6, 7 and 8 for cyclosporine, clarithromycin, ketoconazole, verapamil ER, diltiazem and azithromycin, respectively.

TABLE 1

Incidence of Adverse Effects for Colchicine when Coadministered with Various Inhibitors.

| Safety Criteria | Result | | | | | | |
| --- | --- | --- | --- | --- | --- | --- | --- |
| | Cyclosporine | Clarithromycin | Ketoconazole | Ritonavir | Verapamil ER | Diltiazem ER | Azithromycin |
| Number of 24 subjects with adverse events overall | 6 (25.0%) | 14 (58.3) | 10 (41.7) | 5 (20.8) | 14 (58.3) | 14 (58.3) | 11 (45.8) |
| Total number of adverse events | 5 | 26 | 11 | 8 | 22 | 21 | 27 |
| Number of subjects withdrawn for safety reasons | None | None | None | None | None | 1 vomiting | 1 vomiting |

TABLE 2

Comparative Pharmacokinetics for Colchicine when Coadministered with Cyclosporine

| Cyclosporine PARAMETER | ARITHMETIC* or ln-transformed GEOMETRIC** MEANS | | RATIO (%) | 90% CONFIDENCE LIMITS (%) | |
|---|---|---|---|---|---|
| | TREATMENT-2 | TREATMENT-1 | | LOWER | UPPER |
| $C_{max}$ (pg/mL)** | 8,820 | 2,720 | 324.17 | 292.32 | 356.01 |
| $AUC_T$ (pg · h/mL)** | 29,830 | 12,555 | 317.48 | 291.79 | 343.17 |
| $K_{el}$ (hours$^{-1}$)* | 0.038 | 0.147 | 26.07 | 9.14 | 43 |
| $T_{1/2el}$ (hours)* | 20.65 | 6.777 | 104.43 | 88 | 120.85 |
| $CL_{TOT}/F$ (L/h) | 13.42 | 48.24 | 27.82 | 14.78 | 40.87 |

TABLE 3

Comparative Pharmacokinetics for Colchicine when Coadministered with Clarithromycin

| Clarithromycin PARAMETER | ARITHMETIC* or ln-transformed GEOMETRIC** MEANS | | RATIO (%) | 90% CONFIDENCE LIMITS (%) | |
|---|---|---|---|---|---|
| | TREATMENT-2 | TREATMENT-1 | | LOWER | UPPER |
| $C_{max}$ (pg/mL)** | 8,440 | 2,840 | 297.49 | 277.65 | 317.33 |
| $AUC_T$ (pg · h/mL)** | 41,950 | 12,370 | 339.21 | 314.64 | 363.78 |
| $K_{el}$ (hours$^{-1}$)* | 0.0296 | 0.1324 | 22.35 | 5.28 | 39.43 |
| $T_{1/2el}$ (hours)* | 30.31 | 8.89 | 340.97 | 277.7 | 404.24 |
| $CL_{TOT}/F$ (L/h) | 12.0 | 46.8 | — | — | — |

TABLE 4

Comparative Pharmacokinetics for Colchicine when Coadministered with Ketoconazole

| Ketoconazole PARAMETER | ARITHMETIC* or ln-transformed GEOMETRIC** MEANS | | RATIO (%) | 90% CONFIDENCE LIMITS (%) | |
|---|---|---|---|---|---|
| | TREATMENT-2 | TREATMENT-1 | | LOWER | UPPER |
| $C_{max}$ (pg/mL)** | 5,270 | 2,780 | 189.52 | 176.37 | 202.67 |
| $AUC_T$ (pg · h/mL)** | 34,380 | 11,990 | 286.75 | 265.75 | 307.85 |
| $K_{el}$ (hours$^{-1}$)* | 0.332 | 0.1491 | 22.29 | 8.05 | 36.52 |
| $T_{1/2el}$ (hours)* | 26.06 | 6.28 | 415.24 | 339.4 | 491.09 |
| $CL_{TOT}/F$ (L/h) | 14.8 | 49.3 | 30.01 | 17.81 | 42.22 |

TABLE 5

Comparative Pharmacokinetics for Colchicine when Coadministered with Ritonavir

| Ritonavir PARAMETER | ARITHMETIC* or ln-transformed GEOMETRIC** MEANS | | RATIO (%) | 90% CONFIDENCE LIMITS (%) | |
|---|---|---|---|---|---|
| | TREATMENT-2 | TREATMENT-1 | | LOWER | UPPER |
| $C_{max}$ (pg/mL)** | 4,990 | 1,870 | 267.08 | 239.71 | 294.45 |
| $AUC_T$ (pg · h/mL)** | 29,050 | 8,410 | 345.32 | 304.35 | 386.29 |
| $K_{el}$ (hours$^{-1}$)* | 0.488 | 0.1666 | 131.83 | 117.25 | 146.41 |
| $T_{1/2el}$ (hours)* | 17.41 | 5.15 | 338.42 | 274.48 | 402.36 |
| $CL_{TOT}/F$ (L/h) | 18.59 | 67.93 | 27.37 | 13 | 41.74 |

TABLE 6

Comparative Pharmacokinetics for Colchicine when Coadministered with Verapamil ER

| Verapamil ER PARAMETER | ARITHMETIC* or ln-transformed GEOMETRIC** MEANS | | RATIO (%) | 90% CONFIDENCE LIMITS (%) | |
|---|---|---|---|---|---|
| | TREATMENT-2 | TREATMENT-1 | | LOWER | UPPER |
| $C_{max}$ (pg/mL)** | 3,850 | 2,970 | 129.72 | 115.29 | 149.88 |
| $AUC_T$ (pg · h/mL)** | 24.64 | 13,090 | 199.29 | 174.69 | 201.88 |
| $K_{el}$ (hours$^{-1}$)* | 0.0480 | 0.1409 | 34.05 | 20.13 | 47.96 |
| $T_{1/2el}$ (hours)* | 17.17 | 4.3 | 274.99 | 239.97 | 310.02 |
| $CL_{TOT}/F$ (L/h) | 21.01 | 43.93 | 47.81 | 37.87 | 57.76 |

TABLE 7

Comparative Pharmacokinetics for Colchicine when Coadministered with Diltiazem ER

| Diltiazem ER PARAMETER | ARITHMETIC* or ln-transformed GEOMETRIC** MEANS | | RATIO (%) | 90% CONFIDENCE LIMITS (%) | |
|---|---|---|---|---|---|
| | TREATMENT-2 | TREATMENT-1 | | LOWER | UPPER |
| $C_{max}$ (pg/mL)** | 2,800 | 2,170 | 129.03 | 108.22 | 149.84 |
| $AUC_T$ (pg · h/mL)** | 12,730 | 10,040 | 176.67 | 146.49 | 206.84 |
| $K_{el}$ (hours$^{-1}$)* | 0.0838 | 0.1589 | 52.76 | 38.24 | 67.27 |
| $T_{1/2el}$ (hours)* | 12.5 | 5.51 | 226.66 | 176.7 | 276.63 |
| $CL_{TOT}/F$ (L/h) | 34.7 | 58.88 | 58.94 | 45.81 | 72.06 |

TABLE 8

Comparative Pharmacokinetics for Colchicine when Coadministered with Azithromycin

| Azithromycin PARAMETER | ARITHMETIC* or ln-transformed GEOMETRIC** MEANS | | RATIO (%) | 90% CONFIDENCE LIMITS (%) | |
|---|---|---|---|---|---|
| | TREATMENT-2 | TREATMENT-1 | | LOWER | UPPER |
| $C_{max}$ (pg/mL)** | 3,050 | 2,740 | 111.15 | 94.01 | 128.99 |
| $AUC_T$ (pg · h/mL)** | 17,160 | 11,980 | 143.3 | 124.85 | 161.75 |
| $K_{el}$ (hours$^{-1}$)* | 0.1426 | 0.147 | 97.02 | 79.03 | 115 |
| $T_{1/2el}$ (hours)* | 6.71 | 6.07 | 110.44 | 79.82 | 141.02 |
| $CL_{TOT}/F$ (L/h) | 35.01 | 50.24 | 69.69 | 57.58 | 81.8 |

Example 2: Clinical Conditions for Single Inhibitors of CYP3A4 or P-gp

The following experimental design was the template for studies reported in Examples 3, 4, 5 and 6. Each investigation was a clinical trial conducted as a one-direction, open-label, drug interaction study to investigate the effects of multiple doses of inhibitors on single-dose pharmacokinetics of colchicine in 12 healthy male volunteers, all of whom completed each study except where noted. Each study was a single center, non-randomized, open-label, one-sequence, crossover study.

The primary objective of each study was to investigate the effect of multiple doses of a potentially interacting drug on the pharmacokinetics of colchicine administered as a single 0.6-mg dose in healthy subjects under fasted conditions. The secondary objective was to assess the safety and tolerability of a single 0.6-mg dose of colchicine administered alone and in combination with multiple-doses of the potentially interacting drug. The test product was a 0.6 mg oral capsule of colchicine (West Ward Pharmaceutical Corp., USA).

Except where noted otherwise the diagnosis and main criteria for inclusion of subjects in each study were: male volunteers, non- or ex-smokers, at least 18 years of age with a body mass index greater than or equal to 18.50 and below 30.00 kg/m$^2$. Subjects were in good health as determined by a medical history, complete physical examination (including vital signs), electrocardiogram (ECG) and the usual clinical laboratory tests (hematology, biochemistry, urinalysis) including negative HIV, Hepatitis B and Hepatitis C tests as well as negative screening for ethanol and drugs of abuse in urine.

The treatment protocol included two colchicine administrations separated by a wash-out of 8 calendar days, as follows, so as to obtain representative blood concentration values with and without the presence of the inhibitor.

Day 1 (Treatment-1): Single dose of 1×0.6 mg of colchicine was orally administered under fasting conditions in the morning.

Days 4 to 8 (5 consecutive days): Single dose of inhibitor drug was orally administered twice daily (once in the morning and once in the evening, 12 hours apart).

Day 9 (Treatment-2): Single dose of 1×0.6 mg of colchicine and single dose of inhibitor drug were orally administered concomitantly under fasting conditions in the morning.

For pharmacokinetic analysis the blood of the subjects was collected in 40 samples each as follows: on Days 1 and 9, a blood sample was collected prior to and 0.25, 0.5, 0.75, 1, 1.25, 1.5, 1.75, 2, 2.5, 3, 4, 6, 8, 12, 16, 24, 36, 48 and 72 hours after colchicine administration. The colchicine content of human plasma was then analyzed by HPLC with MS/MS detection with an assay range of 20.0 pg/mL to 18,000.0 pg/mL (for voriconazole and propafenone) or 20.0 pg/mL to 10,000.0 pg/mL (for fluconazole and cimetidine).

The mathematical model and statistical methods of pharmacokinetic parameters were the following: main absorption and disposition parameters using a non-compartmental approach with a log-linear terminal phase assumption; trapezoidal rule to estimate area under the curve; and terminal phase estimation based on maximizing the coefficient of determination. The pharmacokinetic parameters evaluated in this trial were Cmax, $AUC_T$, $AUG_\infty$, $T_{max}$, $AUC_{T/\infty}$, $K_{el}$, $T_{1/2el}$, $Cl_{TOT}/F$ and Vd/F. Statistical analysis was based on a parametric random ANOVA model of the pharmacokinetic parameters; two-sided 90% confidence interval of the ratio of geometric means for the $C_{max}$, $AUC_T$ and $AUG_\infty$ based on ln-transformed data. The ANOVA model was based on fixed factors and treatment.

Safety was evaluated through assessment of adverse events, standard laboratory evaluations, physical examination (including vital signs) and ECG. Safety was determined by descriptive statistics.

Example 3: Strong Inhibitor of CYP3A4; Non-Inhibitor for P-gp

A study was conducted according to the Example 2 using voriconazole as the inhibitor. Voriconazole is a strong inhibitor of CYP3A4 but not an inhibitor of P-gp. The inhibitor dosage form was an oral 200 mg film-coated capsule of Vfend® (voriconazole, from Roerig, Division of Pfizer Inc., USA).

Voriconazole's safety for coadministration was found to be comparable to observations in the absence of any coadministered drug. The relative incidence of adverse effects coadministration with voriconazole is summarized in Table 9. The comparative plasma concentration results are shown graphically in FIG. 1 and FIG. 2.

TABLE 9

Incidence of Adverse Effects for Colchicine when Coadministered with Voriconazole.

| Safety Criteria | Result |
|---|---|
| Number of subjects experiencing adverse events after Treatment-1 | 7 of 12 (58.3%) |
| Total number of adverse events after Treatment-1 | 20 |
| Number of subjects experiencing adverse events after Treatment-2 | 1 of 12 (8.3%) |
| Total number of adverse events after Treatment-2 | 2 |
| Relative severity of adverse events | Mild to moderate; None severe |
| Number of serious adverse events or deaths | None |
| Number of adverse events requiring medication after Treatment-1 | None |
| Number of subjects withdrawn for safety reasons | None |

It was expected that a strong CYP3A4 inhibitor such as voriconazole would increase the exposure of colchicine. However voriconazole had little effect on colchicine's AUC, and decreased $C_{max}$ by about 20%. Taking into consideration the extent of bioavailability, and the range of mean values for $C_{max}$ and AUC, with and without co-administration with the interacting drug, no major difference in safety was observed: colchicine was generally safe and well tolerated by the subjects. Based on the observed pharmacokinetic results colchicine's dosing regimen does not need to be adjusted with concomitant use of voriconazole. The pharmacokinetic parameters for colchicine in this study follow in Tables 10 and 11.

TABLE 10

Comparative Pharmacokinetics for Colchicine when Coadministered with Voriconazole

| | TREATMENT-2 | | TREATMENT-1 | |
|---|---|---|---|---|
| PARAMETER | MEAN | C.V. (%) | MEAN | C.V. (%) |
| $C_{max}$ (pg/mL) | 2058.2 | 44.9 | 2662.6 | 49.8 |
| ln ($C_{max}$) | 7.5147 | 7.1 | 7.7420 | 7.9 |
| $T_{max}$ (median hours) | 1.50 | 35.4 | 1.38 | 30.8 |
| $AUC_T$ (pg · h/mL) | 20730.8 | 36.9 | 19604.9 | 39.4 |
| ln ($AUC_T$) | 9.8783 | 3.7 | 9.7950 | 4.9 |
| $AUC_\infty$ (pg · h/mL) | 24100.1 | 37.3 | 22357.6 | 40.3 |
| ln ($AUC_\infty$) | 10.0285 | 3.6 | 9.9262 | 4.7 |
| $AUC_{T/\infty}$ (%) | 86.14 | 4.6 | 87.75 | 3.6 |
| $K_{el}$ (hours$^{-1}$) | 0.0227 | 16.5 | 0.0240 | 15.8 |
| $T_{1/2el}$ (hours) | 31.30 | 17.0 | 29.63 | 16.7 |
| $CL_{TOT}/F$ (L/h) | 28.1 | 35.6 | 33.0 | 60.9 |
| $V_D/F$ (L) | 1261.3 | 39.2 | 1345.1 | 49.6 |

TABLE 11

Pharmacokinetic Ranges and Ratios for Colchicine when Coadministered with Voriconazole

| PARAMETER | INTRA-SUBJECT C.V. (%) | GEOMETRIC LSMEANS (pg/mL for $C_{max}$; pg · h/mL for $AUC_T$ and $AUC_\infty$) | | RATIO (%) | 90% CONFIDENCE LIMITS (%) | |
|---|---|---|---|---|---|---|
| | | TREATMENT-2 | TREATMENT-1 | | LOWER | UPPER |
| $C_{max}$ | 30.8 | 1834.9 | 2303.1 | 79.67 | 63.90 | 99.33 |
| $AUC_T$ | 28.0 | 19502.6 | 17943.1 | 108.69 | 88.89 | 132.91 |
| $AUC_\infty$ | 27.2 | 22663.5 | 20459.6 | 110.77 | 91.06 | 134.76 |

Example 4: Moderate Inhibitor of CYP3A4; Non-Inhibitor for P-gp

A study was conducted according to the protocol of Example 2, using fluconazole as the inhibitor. Fluconazole is a moderate inhibitor of CYP3A4 but not an inhibitor of P-gp. The inhibitor dosage form was an oral 200 mg tablet of Diflucan® (fluconazole, from Pfizer).

The fluconazole trial differed from the Example 2 protocol as follows. The subject inclusion criteria did not exclude smokers. And instead of twice-daily doses (12 hours apart) of inhibitor drug on days 4 to 8, subjects instead received a double dose on the morning of day 4 (a loading dose) and a once-daily dose administered in the mornings of each of days 5 to 8.

The safety of colchicine when coadministered with voriconazole was comparable to observations in the absence of any coadministered drug. The relative incidence of adverse effects during coadministration with fluconazole is summarized in Table 12. The comparative plasma concentration results are shown graphically in FIG. 3 and FIG. 4.

As a moderate inhibitor of CYP3A4 fluconazole was expected to significantly increase the maximum concentration of colchicine in the blood. With co-administration of fluconazole the mean $C_{max}$ for colchicine increased by only 13%; overall exposure of colchicine (AUC) increased by somewhat more (40%). Taking into account the extent of bioavailability, and the range of mean values for $C_{max}$ and AUC, the safety impact appears to be acceptable and no major difference in safety was observed: colchicine was generally safe and well tolerated by the subjects included in this study. Based on the observed pharmacokinetic results colchine's dosing regimen may remain unchanged with concomitant use of fluconazole. The pharmacokinetic parameters for colchicine in this study follow in Tables 13 and 14.

TABLE 12

Incidence of Adverse Effects for Colchicine when Coadministered with Fluconazole

| Safety Criteria | Result |
| --- | --- |
| Number of subjects experiencing adverse events after Treatment-1 | 3 of 12 (25.0%) |
| Total number of adverse events after Treatment-1 | 7 |
| Number of subjects experiencing adverse events after Treatment-2 | 3 of 12 (25.0%) |
| Total number of adverse events after Treatment-2 | 3 |
| Relative severity of adverse events | Mild to moderate; None severe |
| Number of serious adverse events or deaths | None |
| Number of adverse events requiring medication after Treatment-1 | None |
| Number of subjects withdrawn for safety reasons | None |

TABLE 13

Comparative Pharmacokinetics for Colchicine when Coadministered with Fluconazole

| | TREATMENT-2 | | TREATMENT-1 | |
| --- | --- | --- | --- | --- |
| PARAMETER | MEAN | C.V. (%) | MEAN | C.V. (%) |
| $C_{max}$ (pg/mL) | 2299.2 | 57.6 | 1925.6 | 34.6 |
| ln ($C_{max}$) | 7.6238 | 6.3 | 7.5020 | 5.0 |
| $T_{max}$ (median hours) | 1.38 | 25.4 | 1.25 | 32.8 |
| $AUC_T$ (pg · h/mL) | 21270.7 | 33.6 | 14939.4 | 25.5 |
| ln ($AUC_T$) | 9.9215 | 3.0 | 9.5793 | 2.9 |
| $AUC_\infty$ (pg · h/mL) | 25586.1 | 35.5 | 17477.7 | 24.7 |
| ln ($AUC_\infty$) | 10.1018 | 3.1 | 9.7384 | 2.7 |
| $AUC_{T/\infty}$ (%) | 83.54 | 2.9 | 85.33 | 3.1 |
| $K_{el}$ (hours$^{-1}$) | 0.0204 | 13.3 | 0.0206 | 11.6 |
| $T_{1/2el}$ (hours) | 34.51 | 14.8 | 34.05 | 12.2 |
| $CL_{TOT}/F$ (L/h) | 25.6 | 28.2 | 36.6 | 28.6 |
| $V_D/F$ (L) | 1250.5 | 24.7 | 1807.7 | 32.1 |

TABLE 14

Pharmacokinetic Ranges and Ratios for Colchicine when Coadministered with Fluconazole

| PARAM-ETER | INTRA-SUBJECT C.V. (%) | GEOMETRIC LSMEANS * (pg/mL for $C_{max}$ and pg · h/mL for $AUC_T$ and $AUC_\infty$) | | RATIO (%) | 90% CONFIDENCE LIMITS (%) | |
| --- | --- | --- | --- | --- | --- | --- |
| | | TREATMENT-2 | TREATMENT-1 | | LOWER | UPPER |
| $C_{max}$ | 27.1 | 2046.3 | 1811.7 | 112.95 | 92.90 | 137.33 |
| $AUC_T$ | 22.4 | 20364.2 | 14461.6 | 140.82 | 119.70 | 165.65 |
| $AUC_\infty$ | 22.5 | 24386.8 | 16955.6 | 143.83 | 122.18 | 169.30 |

Example 5: Weak Inhibitor of CYP3A4; Non-Inhibitor for P-gp

A study was conducted according to the protocol of Example 2, using cimetidine as the inhibitor. Cimetidine is a weak inhibitor of CYP3A4 but not an inhibitor of P-gp. The inhibitor dosage form was an oral 800 mg film-coated tablet USP of cimetidine (Mylan Pharmaceuticals Inc., USA).

The cimetidine trial differed from the template protocol as follows. The subject inclusion criteria did not exclude females but did require that they test negative for pregnancy. And instead of twice-daily doses (12 hours apart) of inhibitor drug on days 4 to 8, subjects instead received a double dose on the morning of day 4 (a loading dose) and a once-daily dose administered in the mornings of each of days 5 to 8.

Cimetidine's safety for coadministration was found to be comparable to observations in the absence of any coadministered drug. The relative incidence of adverse effects from coadministration with cimetidine is summarized in Table 15. The comparative plasma concentration results are shown graphically in FIG. 5 and FIG. 6.

It was expected that a weak CYP3A4 inhibitor such as cimetidine would have a small effect on the exposure of colchicine. Unexpectedly cimetidine actually modestly decreased the peak plasma concentration of colchicine below levels observed without coadministration: colchicine $C_{max}$ was lower by 33% and AUC was lower by 15%, though this was not significant.

Taking into consideration the extent of bioavailability, and the range of mean values for $C_{max}$ and AUC, the safety impact appears to be acceptable and no major difference in safety would be expected with and without co-administration with cimetidine: colchicine was generally safe and well tolerated by the subjects included in this study. Based on the observed pharmacokinetic results colchine's dosing regimen may remain unchanged with concomitant use of cimetidine. The pharmacokinetic parameters for colchicine follow in Tables 16 and 17.

TABLE 15

Incidence of Adverse Effects for Colchicine when Coadministered with Cimetidine.

| Safety Criteria | Result |
| --- | --- |
| Number of subjects experiencing adverse events after Treatment-1 | 7 of 12 (58.3%) |
| Total number of adverse events after Treatment-1 | 11 |
| Number of subjects experiencing adverse events after Treatment-2 | 1 of 12 (8.3%) |
| Total number of adverse events after Treatment-2 | 2 |
| Relative severity of adverse events | Mild to moderate; None severe |
| Number of serious adverse events or deaths | None |
| Number of adverse events requiring medication after Treatment-1 | None |
| Number of subjects withdrawn for safety reasons | None |

TABLE 16

Comparative Pharmacokinetics for Colchicine when Coadministered with Cimetidine

| | TREATMENT-2 | | TREATMENT-1 | |
| --- | --- | --- | --- | --- |
| PARAMETER | MEAN | C.V. (%) | MEAN | C.V. (%) |
| $C_{max}$ (pg/mL) | 2108.7 | 50.2 | 2996.8 | 38.6 |
| ln ($C_{max}$) | 7.5380 | 6.7 | 7.9318 | 5.3 |
| $T_{max}$ (median hours) | 1.03 | 30.2 | 1.25 | 20.9 |
| $AUC_T$ (pg·h/mL) | 18082.1 | 41.6 | 20382.1 | 38.8 |
| ln ($AUC_T$) | 9.7243 | 4.3 | 9.8658 | 3.4 |
| $AUC_\infty$ (pg·h/mL) | 21038.3 | 43.6 | 24000.7 | 39.2 |
| ln ($AUC_\infty$) | 9.8696 | 4.4 | 10.0263 | 3.5 |
| $AUC_{T/\infty}$ (%) | 86.53 | 3.6 | 85.29 | 5.2 |
| $K_{el}$ (hours$^{-1}$) | 0.0222 | 11.2 | 0.0201 | 16.9 |
| $T_{1/2el}$ (hours) | 31.54 | 11.1 | 35.46 | 19.3 |
| $CL_{TOT}/F$ (L/h) | 33.8 | 43.4 | 27.9 | 30.8 |
| $V_D/F$ (L) | 1513.4 | 41.1 | 1410.8 | 31.3 |

TABLE 17

Pharmacokinetic Ranges and Ratios for Colchicine when Coadministered with Cimetidine

| PARAMETER | INTRA-SUBJECT C.V. (%) | GEOMETRIC LSMEANS (pg/mL for $C_{max}$ and pg·h/mL for $AUC_T$ and $AUC_\infty$) | | RATIO (%) | 90% CONFIDENCE LIMITS (%) | |
| --- | --- | --- | --- | --- | --- | --- |
| | | TREATMENT-2 | TREATMENT-1 | | LOWER | UPPER |
| $C_{max}$ | 29.3 | 1878.1 | 2784.5 | 67.45 | 54.65 | 83.25 |
| $AUC_T$ | 18.7 | 16719.0 | 19260.8 | 86.80 | 75.78 | 99.43 |
| $AUC_\infty$ | 19.4 | 19334.3 | 22612.3 | 85.50 | 74.29 | 98.41 |

Example 6: Inhibitor of P-gp; Non-Inhibitor for CYP3A4

A study was conducted according to the protocol of Example 2, using propafenone as the inhibitor. Propafenone is an inhibitor of P-gp but not of CYP3A4. The inhibitor dosage form was an oral 225 mg film-coated tablet of Rythmol® (propafenone, from Halo Pharmaceutical Inc., USA for GlaxoSmithKline, USA).

The fluconazole trial differed from the Example 2 protocol as follows. Subjects were included only if they were not older than 45 years (as opposed to no upper limit). Also, in inclusion criteria the lower threshold for the body mass index was 21.00 (as opposed to 18.00) kg/m$^2$. Of the 12 subjects who began the study 3 dropped out for reasons unrelated to the investigation.

Propafenone's safety for coadministration was found to be comparable to observations in the absence of any coadministered drug. The relative incidence of adverse effects when colchicine was coadministered with propafenone is summarized in Table 18. The comparative plasma concentration results are shown graphically in FIG. 7 and FIG. 8.

It was expected that propafenone, being an inhibitor of colchicine transport/export by P-gp would increase the exposure of colchicine. But propafenone had almost no effect on either colchicine's $C_{max}$ or AUC: for $C_{max}$ and AUC, an increase of only 7% and 1% respectively was observed. Taking into consideration the extent of bioavailability, and the range of mean values for $C_{max}$ and AUC, with and without co-administration with the interacting drug, no major difference in safety was observed: colchicine was generally safe and well tolerated by the subjects. Based on the observed pharmacokinetic results colchicine's dosing regimen does not need to be adjusted with concomitant use of propafenone. The pharmacokinetic parameters for colchicine follow in Tables 19 and 20.

TABLE 18

Incidence of Adverse Effects for Colchicine when Coadministered with Propafenone

| Safety Criteria | Result |
| --- | --- |
| Number of subjects experiencing adverse events after Treatment-1 | 9 of 12 (75.0%) |
| Total number of adverse events after Treatment-1 | 19 |
| Number of subjects experiencing adverse events after Treatment-2 | 1 of 12 (8.3%) |
| Total number of adverse events after Treatment-2 | 1 |
| Relative severity of adverse events | Mild to moderate; None severe |
| Number of serious adverse events or deaths | None |
| Number of adverse events requiring medication after Treatment-1 | None |
| Number of subjects withdrawn for safety reasons | None |

TABLE 19

Comparative Pharmacokinetics for Colchicine when Coadministered with Propafenone

| PARAMETER | TREATMENT-2 MEAN | TREATMENT-2 C.V. (%) | TREATMENT-1 MEAN | TREATMENT-1 C.V. (%) |
| --- | --- | --- | --- | --- |
| $C_{max}$ (pg/mL) | 2206.0 | 17.3 | 2117.5 | 26.6 |
| ln ($C_{max}$) | 7.6861 | 2.2 | 7.6252 | 3.6 |
| $T_{max}$ (median hours) | 1.00 | 39.5 | 1.50 | 23.0 |
| $AUC_T$ (pg · h/mL) | 16777.6 | 22.9 | 16626.1 | 21.8 |
| ln ($AUC_T$) | 9.7059 | 2.3 | 9.6956 | 2.4 |
| $AUC_\infty$ (pg · h/mL) | 18864.3 | 24.3 | 18928.3 | 23.0 |
| ln ($AUC_\infty$) | 9.8211 | 2.3 | 9.8221 | 2.6 |
| $AUC_{T/\infty}$ (%) | 89.16 | 3.4 | 88.21 | 5.0 |
| $K_{el}$ (hours$^{-1}$) | 0.0250 | 13.6 | 0.0241 | 16.6 |
| $T_{1/2el}$ (hours) | 28.25 | 15.4 | 29.74 | 21.5 |
| $CL_{TOT}$/F (L/h) | 33.3 | 20.9 | 33.5 | 27.7 |
| $V_D$/F (L) | 1359.0 | 28.1 | 1410.2 | 24.7 |

TABLE 20

Pharmacokinetic Ranges and Ratios for Colchicine when Coadministered with Propafenone

| PARAMETER | INTRA-SUBJECT C.V. (%) | GEOMETRIC LSMEANS (pg/mL for $C_{max}$ and pg · h/mL for $AUC_T$ and $AUC_\infty$) TREATMENT-2 | GEOMETRIC LSMEANS TREATMENT-1 | RATIO (%) | 90% CONFIDENCE LIMITS (%) LOWER | 90% CONFIDENCE LIMITS (%) UPPER |
| --- | --- | --- | --- | --- | --- | --- |
| $C_{max}$ | 23.0 | 2178.0 | 2049.3 | 106.28 | 87.07 | 129.73 |
| $AUC_T$ | 20.5 | 16413.7 | 16245.3 | 101.04 | 84.57 | 120.71 |
| $AUC_\infty$ | 20.0 | 18418.2 | 18437.2 | 99.90 | 83.95 | 118.87 |

In summary the present invention supports the safe use of conventional doses of colchicine in combination with conventional doses of a second drug that treats another medical condition but also inhibits one of either CYP3A4 or P-gp but not both. The present invention thus allows colchicine to be dosed at safe and effective levels when coadministered with these drugs.

Those skilled in the art will appreciate that the present invention has a wide range of applications and that it fulfills the needs of the prior art described herein and meets the above-stated objects. While there has been shown and described preferred embodiments of the invention, it will be evident to those skilled in the art that various modifications and changes may be made thereto without departing from the spirit and the scope of the invention as set forth in the appended claims and equivalence thereof.

The invention claimed is:

1. A method of administering colchicine to a patient in need thereof while concomitantly administering a second drug that is an inhibitor of P-glycoprotein 1 (P-gp) but is not an inhibitor of the cytochrome P450 3A4 isozyme (CYP3A4), wherein the second drug is propafenone, wherein the method comprises:
   (a) administering to the patient a fixed maintenance dose of colchicine in an amount of from about 0.6 to about 1.2 mg/day, for a maintenance period of a plurality of days, without administering propafenone;
   (b) after step (a), administering to the patient one or more therapeutically effective doses of the second drug; and
   (c) concomitantly with step (b), administering to the patient the fixed maintenance dose of colchicine of step (a) without dose reduction.

2. The method of claim 1, wherein the second drug is administered at a dose of from 225 mg/day to 450 mg/day.

3. The method of claim 1, wherein the fixed maintenance dose of colchicine is 0.6 mg/day.

4. The method of claim 1, wherein the fixed maintenance dose of colchicine is 1.2 mg/day.

5. The method of claim 1, wherein the plurality of days comprises at least 7 days.

6. The method of claim 1, wherein step (b) is performed after step (a).

7. The method of claim 1, wherein the colchicine is administered to the patient for the prevention of gout flares.

8. A method of preventing gout flares in a patient in need thereof comprising administering colchicine while concomitantly administering a second drug that is an inhibitor of P-glycoprotein 1 (P-gp) but is not an inhibitor of the cytochrome P450 3A4 isozyme (CYP3A4), wherein the second drug is propafenone, wherein the method comprises:
   (a) administering to the patient a fixed maintenance dose of colchicine in an amount of from about 0.6 to about 1.2 mg/day, for a maintenance period of a plurality of days, without administering propafenone;
   (b) after step (a), administering to the patient one or more therapeutically effective doses of the second drug; and
   (c) concomitantly with step (b), administering to the patient the fixed maintenance dose of colchicine of step (a) without dose reduction.

9. The method of claim 8, wherein the second drug is administered at a dose of from 225 mg/day to 450 mg/day.

10. The method of claim 8, wherein the fixed maintenance dose of colchicine is 0.6 mg/day.

11. The method of claim 8, wherein the fixed maintenance dose of colchicine is 1.2 mg/day.

12. The method of claim 8, wherein the plurality of days comprises at least 7 days.

13. The method of claim 8, wherein step (b) is performed after step (a).

* * * * *

UNITED STATES PATENT AND TRADEMARK OFFICE
CERTIFICATE OF CORRECTION

| | | |
|---|---|---|
| PATENT NO. | : 9,675,613 B2 | Page 1 of 1 |
| APPLICATION NO. | : 14/511703 | |
| DATED | : June 13, 2017 | |
| INVENTOR(S) | : Murray Ducharme | |

It is certified that error appears in the above-identified patent and that said Letters Patent is hereby corrected as shown below:

In the Specification

Column 19, Line 22: Delete "$AUG_\infty$" and insert --$AUC_\infty$--

Column 19, Line 26: Delete "$AUG_\infty$" and insert --$AUC_\infty$--

Signed and Sealed this
Eighth Day of August, 2017

Joseph Matal
*Performing the Functions and Duties of the*
*Under Secretary of Commerce for Intellectual Property and*
*Director of the United States Patent and Trademark Office*